US006983208B2

(12) United States Patent
Metcalf et al.

(10) Patent No.: US 6,983,208 B2
(45) Date of Patent: Jan. 3, 2006

(54) METHOD AND APPARATUS FOR COMBINED MEASUREMENTS OF CONCENTRATION, DISTRIBUTION AND FLOW VELOCITY OF SUSPENDED SOLIDS

(75) Inventors: Michael A. Metcalf, San Diego, CA (US); John M. Land, Godalming (GB)

(73) Assignee: MGD Technologies, Inc., San Diego, CA (US)

( * ) Notice: Subject to any disclaimer, the term of this patent is extended or adjusted under 35 U.S.C. 154(b) by 116 days.

(21) Appl. No.: 10/722,046

(22) Filed: Nov. 24, 2003

(65) Prior Publication Data

US 2005/0114046 A1    May 26, 2005

(51) Int. Cl.
  G01F 1/00   (2006.01)
  G01F 17/00  (2006.01)
  G01F 1/20   (2006.01)
  G01F 1/66   (2006.01)

(52) U.S. Cl. ............................ 702/45; 702/48; 702/54; 73/861.18; 73/861.25

(58) Field of Classification Search ................ 702/45, 702/48, 50, 54, 128; 73/861.18, 861.21, 73/861.25, 861.26
See application file for complete search history.

(56) References Cited

U.S. PATENT DOCUMENTS 5,343,443 A    8/1994   Merewether
RE35,535 E    6/1997   Brumley et al.
5,777,892 A *  7/1998   Nabity et al. ................ 702/143

* cited by examiner

Primary Examiner—John Barlow
Assistant Examiner—Meagan S Walling
(74) Attorney, Agent, or Firm—Charmasson, Buchaca & Leach, LLP

(57) ABSTRACT

A remote sensor and associated data processor, performs concurrent analysis of backscattered signals from a multi-beam acoustic Doppler emitter/receiver positioned against the inside wall of a conveying pipe or channel. Range-gating of the return signals allows independent analysis of discrete volumes of backscattered signal data corresponding to the distribution, concentration and travel velocity of small individual volumes or bins of water and suspended solids. Velocity is derived from the measured Doppler frequency shift for each bin. Relative solids concentration is estimated as a function of the measured intensity of the backscattered signals. The intensity data are calibrated by inputting site-specific environmental information, such as temperature, salinity, acoustical system constant, backscattered signal interpretation ratio between concentration and particle size, and concurrently measured concentration values obtained from physical sample collection and previous laboratory analysis into the analytical computer program. The program uses iterative routines that adjust calibration parameters using data obtained from the previous measurement on an adjacent layer in a continuous self-correcting process. The apparatus and method provide both historical and real-time measurements of distribution, concentration and velocity of suspended solids in a flow of piped or channeled liquid.

40 Claims, 5 Drawing Sheets

METHOD AND APPARATUS FOR COMBINED MEASUREMENTS OF CONCENTRATION, DISTRIBUTION AND FLOW VELOCITY OF SUSPENDED SOLIDS

FIELD OF THE INVENTION

This invention relates to measurement of water quality, and more specifically to instruments used for measuring the concentration of suspended solids in a liquid flowing through a conduit.

BACKGROUND OF THE INVENTION

The safe disposal of sewer effluents and water treatment requires measurements of suspended solid concentration in treatment pipes, culverts and other conduits.

A sewer effluent containing a low value of suspended solids may be subject to a reduced treatment or no treatment at all. A plant treating sewer effluents from several municipalities may bill those municipalities in accordance with the volume flow and the total suspended solids concentration measured on the intake conduits from each municipality.

In the past, intrusive periodical samplings of solids-carrying water were taken and analyzed in laboratories to provide needed information about the solids content of the water.

Various methods have been proposed to electronically measure total solids concentration in a volume of liquid, but no instrumentation has been provided for concurrently measuring suspended solids concentration as well as flow on a continuous, real time base.

This invention results from an attempt to provide a more practical instrumentation for use in sewer and water collection systems, distribution systems and treatment plants.

SUMMARY OF THE INVENTION

The principal and secondary objects of this invention are to provide a method and apparatus for continuously measuring the total solids concentration in a liquid flowing through a pipe or conduit as well as the speed of various layers of flow within that pipe and calculating flow rate.

These and other valuable objects are achieved by placing an acoustical transmitter on the inside wall of a pipe or other conduit. The transmitter emits two pairs of obliquely divergent beams, one beam of each pair is aimed downstream from the other one in the pair. Echo signals of the emitted waveform are divided into sampling periods corresponding to discrete volumes of the liquid in the pipe distributed along each beam. Doppler frequency shifts received from the beams are interpreted into velocity measurements of the suspended solids assumed to be flowing ambiently with the water within a number of flow layers within the pipe. The intensity of the backscattered echo signals are translated into solids concentration values using in sita calibration measurements and simplified algorithms, combined with iterative routines that adjust calibration parameters using data obtained from previous measurements on an adjacent layer in a continuous self-correcting process.

DESCRIPTION OF THE PREFERRED EMBODIMENT OF THE INVENTION

Figure 1:
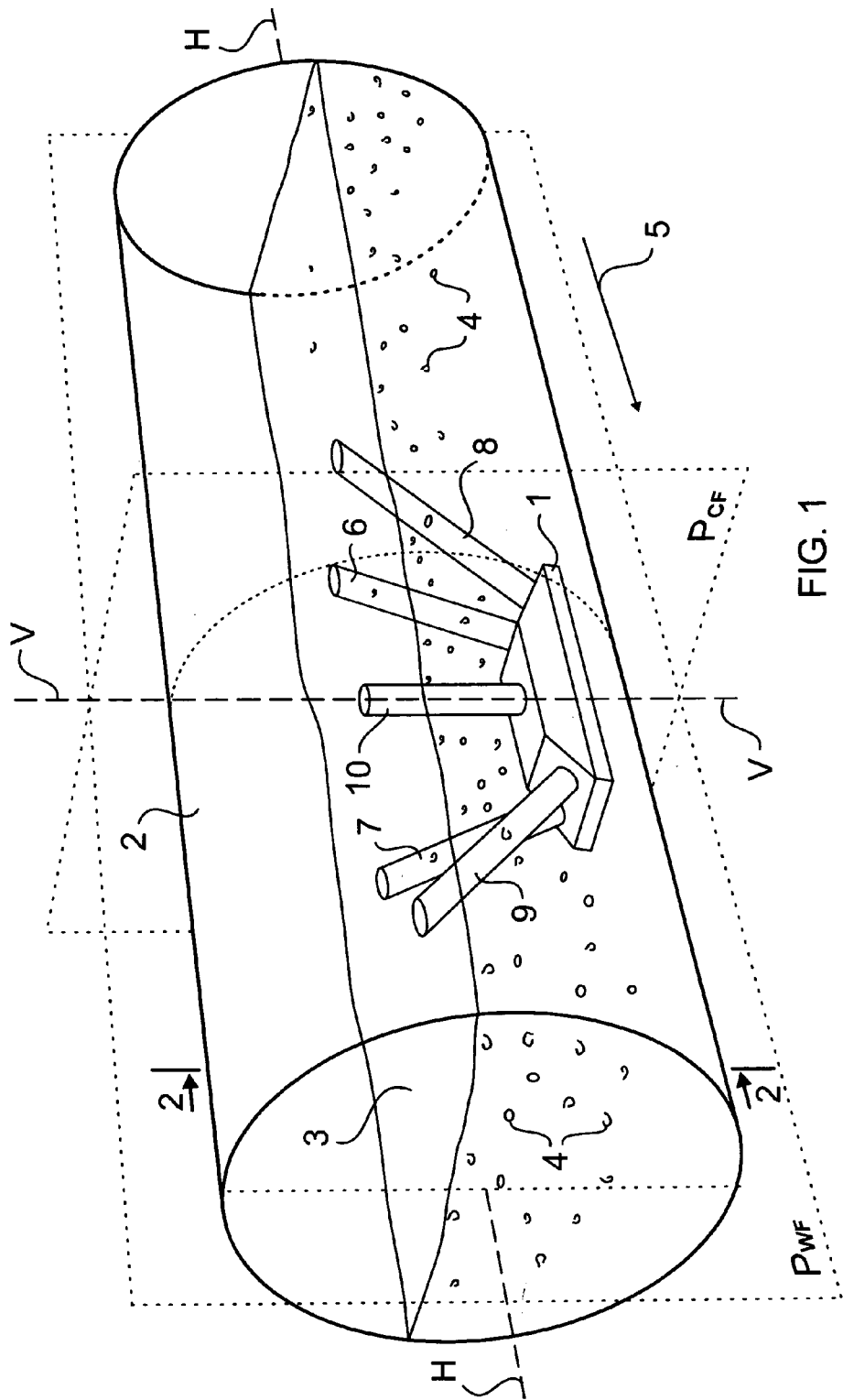
FIG. 1 is a diagrammatical perspective view of a conduit equipped with a flow and concentration measuring transducer.
Figure 2:
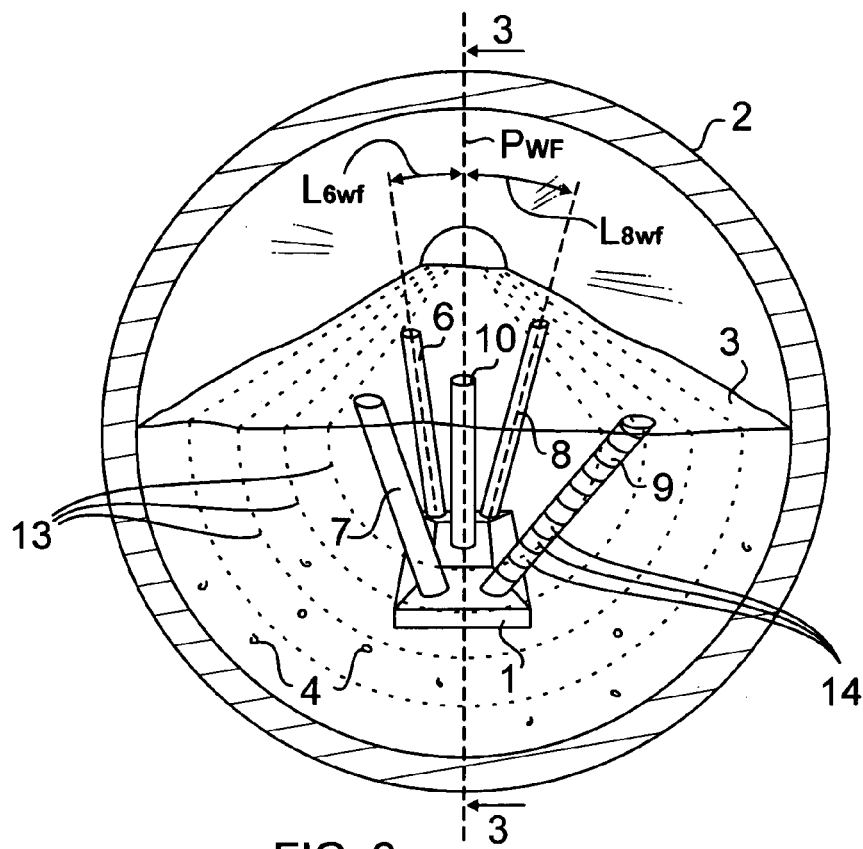
FIG. 2 is a diagrammatical cross-sectional view of the conduit of FIG. 1 taken along line 2—2 thereof.
Figure 3:
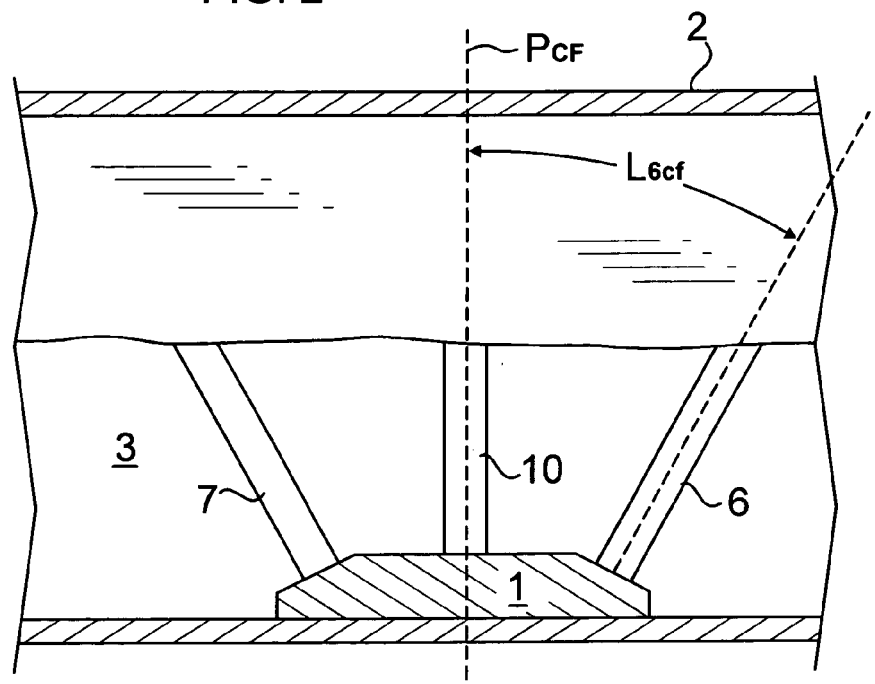
FIG. 3 is a diagrammatical cross-sectional view of the conduit of FIG. 1 taken along line 3—3.

Referring now to the drawing, there is shown in FIGS. 1–3, a suspended solids velocity and concentration transducer 1 installed at the bottom of a pipe 2 carrying water 3 containing suspended solids 4 and flowing in the direction indicated by the arrow 5 in FIG. 1. Orientations within the pipe can be specified by reference to the relative horizontal axis H which would be the central major axis of the generally cylindrical pipe and relative vertical axis V which is perpendicular to H and substantially normal to the surface of the water. The plane $P_{WF}$ is aligned vertically with the flow and contains both V and H axes. The plane $P_{CF}$ is aligned vertically across the flow containing the V axis and perpendicular to the H axis. Piezoelectric ceramics in the transducer emit an acoustical waveform consisting of short pulses along four narrow beams 6, 7, 8, 9 pointing in different directions. The beams are grouped into two pairs.

The first pair 6, 7 has a first upstream beam 6 oriented at a first angle $L_{6cf}$ from the cross-flow plane $P_{CF}$ tending into the flow and a second angle $L_{6wf}$ from the with-flow plane $P_{WF}$ tending toward the side wall of the pipe.

The first angle $L_{6cf}$ is preferably between about 5 and 80 degrees, more preferably 10 and 30 degrees, and most preferably about 20 degrees. The second angle $L_{6wf}$ is preferably between about 0 and 60 degrees, more preferably between about 0 and 30 degrees, and most preferably about 10 degrees.

The first pair has a second down stream beam 7 oriented in a mirror image of the first beam 6 about the cross-flow plane $P_{CF}$.

The second pair 8, 9 has a first upstream beam 8 oriented at a first angle $L_{8cf}$ from the cross-flow plane $P_{CF}$ tending into the flow and a second angle $L_{8wf}$ from the with-flow plane $P_{WF}$ tending toward the side wall of the pipe.

The first angle $L_{8cf}$ is preferably between about 5 and 80 degrees, more preferably 20 and 60 degrees and most preferably about 30 degrees. The second angle $L_{8wf}$ is preferably between about 0 and 60 degrees, more preferably between about 0 and 30 degrees and most preferably about 10 degrees.

The second pair has a second down stream beam 9 oriented in a mirror image of the first beam 8 about the cross flow plane $P_{CF}$.

As more specifically shown in FIG. 2, each pair of beams preferably lie within a plane which is aimed at a transversal angle from the vertical and from the other pair of beams. Echo signals of the pulses are backscattered from the suspended solids 4. Since these solids have motion relative to the transducer, the echo signals are Doppler-shifted in frequency. A fifth ceramic transducer 10 mounted in the center of the transducer and aimed vertically is used to measure the depth of flow.

Figure 4:
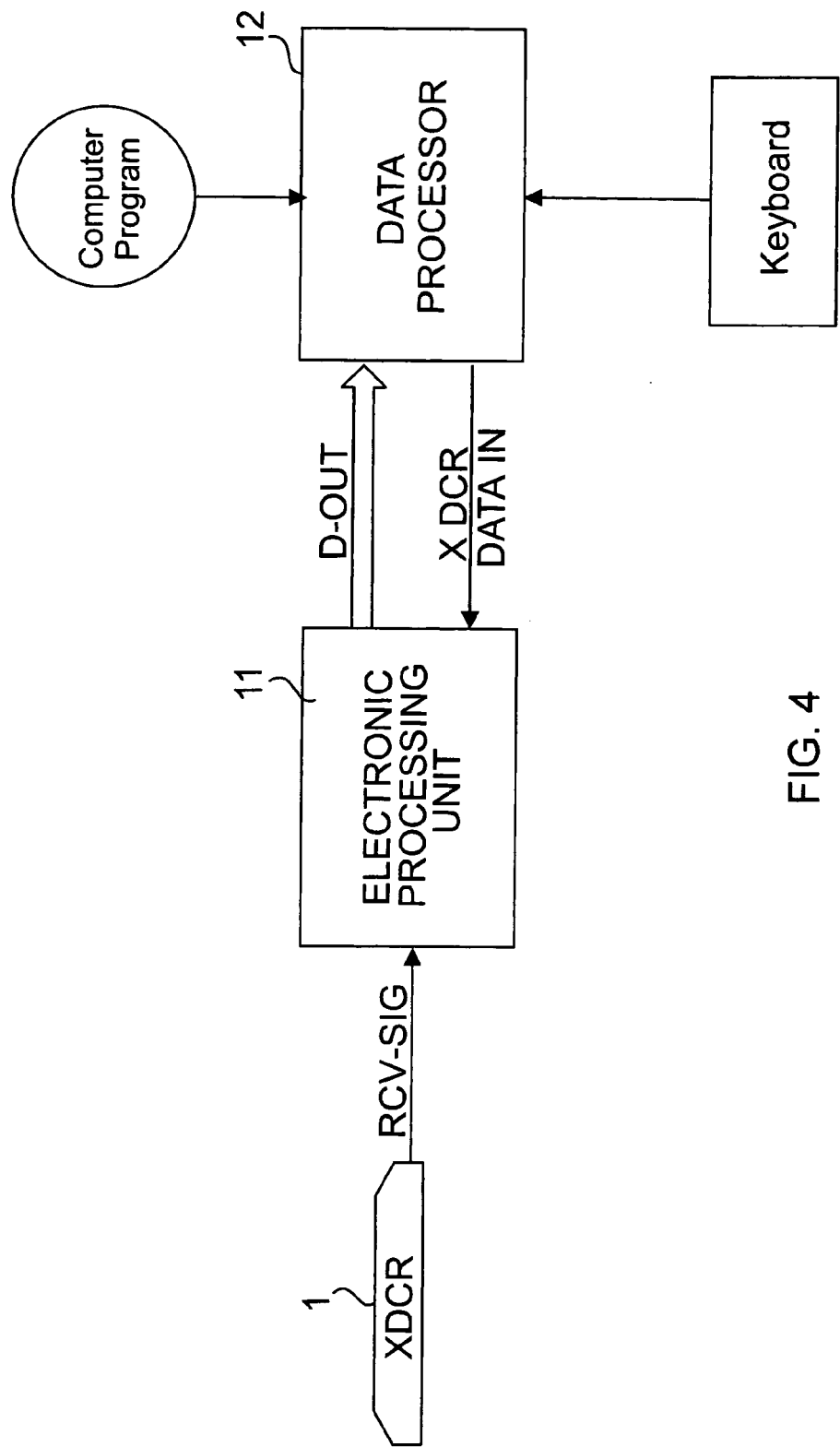
FIG. 4 is a block diagram of the concentration, distribution and flow velocity measurement instrument.
Figure 5:
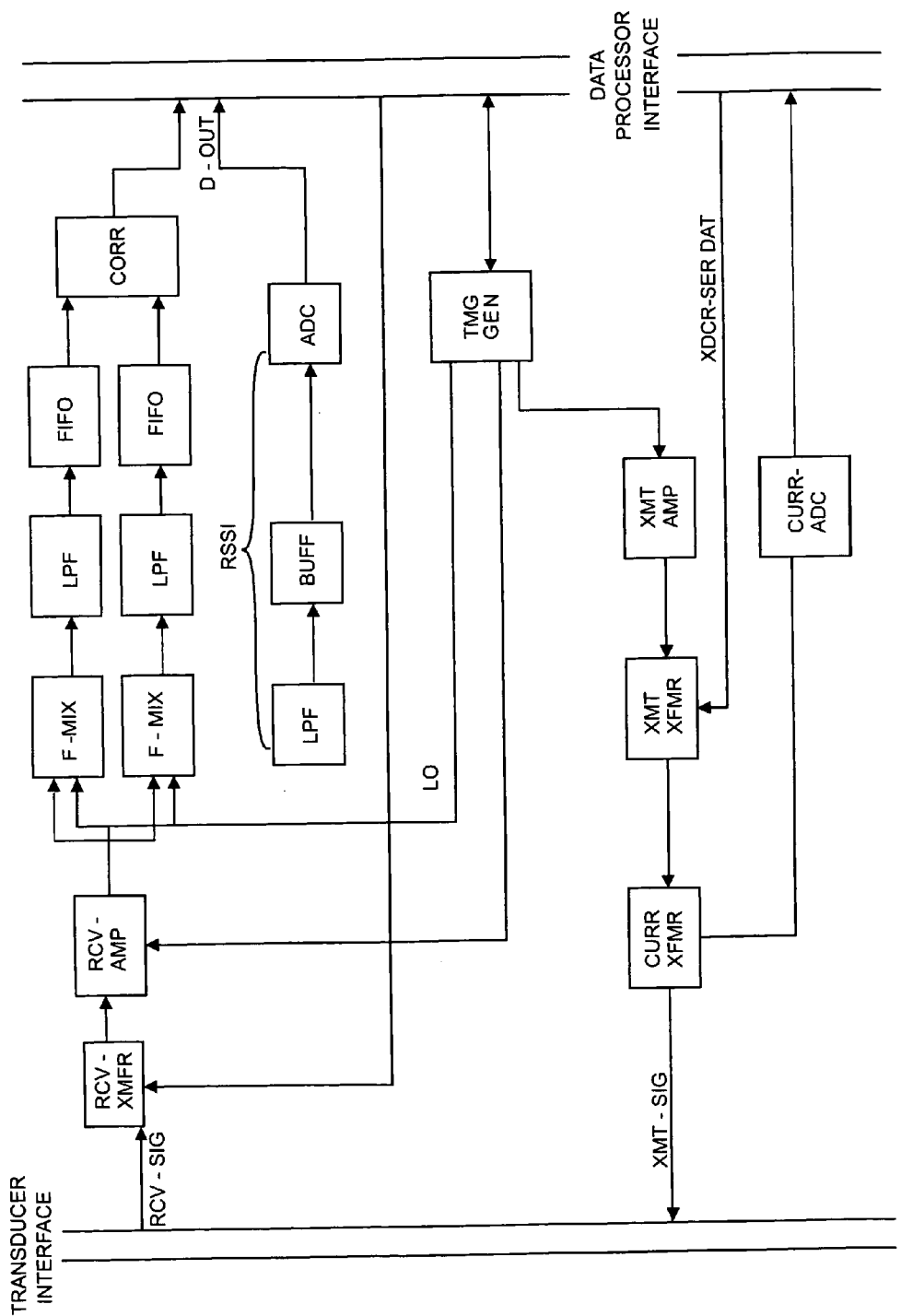
FIG. 5 is a block diagram of the electronic processing unit.

As illustrated in FIGS. 4 and 5, the system includes an electronic processing unit 11 that receives an input signal RCVS-SIG from the transducer 1 and converts it into digital data D-OUT that is fed to a data processor 12. The system divides the echo signals into discrete regular intervals for samplings that correspond to different, discrete volumes at different ranges of the flowing liquid. Velocity is calculated from the frequency shift measured in each sampling. The result is a profile of linear distribution of velocity along the beams illustrated by velocity profile lines 13 in FIG. 2. Each of the small divisions 14 shown along beam 9 of FIG. 2 represent an individual velocity measurement in a discrete volume known as a depth cell or bin. The velocity profile lines 13 are generated from velocity data measured by the upstream and downstream beam of each pair.

Since Doppler measurements are directional, only the component velocity along the direction of transmit and receive is measured. Narrow acoustic beams are used to accurately determine the horizontal velocity of the flow. The accuracy of the measurement is also enhanced by using gating times for the samplings that correspond to small volumes of a minimum size of approximately 5 centimeters in length and 4 centimeters in diameter and approximately $\frac{1}{25}$ of the beam length to conduit wall. Potential bias in the return energy spectrum due to range dependent variables is avoided. The result is a very precise measurement of the vertical and transversal distribution of flow velocities. The velocity data from the two pairs of beams are entered into an algorithm to determine a mathematical discription of the flow velocities throughout the entire cross-section of the liquid. The algorithm fits the basic funtions of a parametric model to the actual data. The results predicts flow velocity at all points throughout the liquid. These results are integrated over the cross-sectional area to determine the discharge.

The key benefit of this approach is that the system will operate accurately under different hydraulic conditions. As hydraulic conditions change, the change will manifest itself in the distribution of velocity throughout the depth of flow. As the system is measuring the velocity distribution directly, it will adapt to the changes in hydraulics, and generate a flow pattern that is representative of the new hydraulic conditions, insuring an accurate calculation of the flow rate.

The measurement of distribution and concentration of the suspended solids 4 stems from a requirement of the frequency measurement circuits within the electronic processing unit 11 to receive a near-constant input voltage. An acoustic pulse emitted from the transducer 1 has a certain initial intensity that progressively diminishes as it travels through the liquid and is scattered from suspended particles. The reflected energy detected by the transducer is a very small fraction of that which was emitted. In addition, the return intensity of the backscattered echoes vary considerably according to, but not limited to, the range to the point of energy reflection, the concentration of reflecting particles, and the water temperature. The received weakened signal RCV-SIG passes through an amplifier RCV-AMP that brings it to the level required by the frequency measurement circuits. A large loss of signal strength requires a large degree of amplification. The degree of amplification which is required is thus a measure of the loss of signal strength and, inversely, a measure of the intensity of the backscatter. The amount of amplification required is provided by the Receive Signal Strength Indicator RSSI. It is this measurement which facilitates the estimation of suspended solid concentration in the water column. In other words, the intensity value of the backscattered signal is translated into concentration values of the suspended solids using the data processor 12 and the frequency shifts of the receive signal are interpreted as an indication of velocity of the solids in the flow of liquid.

The transducer output signal RCV-SIG is routed to a receive coupling transformer RCV-XFMR that provides isolation and impedance matching. The signal is further amplified and bandwidth limited by the high gain selective log amplifier RCV-AMP. The amplified receive signal is fed to a pair of frequency mixers FMIX, where the signal is mixed replicatively with the local oscillator signal frequency LO. The desired base band signal, which is the difference frequency of the receive signal and the local oscillator frequency, is obtained by passing the mixer output signals through a pair of low pass filters LPF. The base band signals contain now the entire Doppler spectrum without the carrier signal. The mixers, are quadrature mixers, where an in-phase and a quadrature signal are obtained. Both signals are needed for the correlator CORR, which performs the basic digital signal processing. The in-phase and quadrature signals are buffered by a pair of first-in/first-out buffers FIFO and become part of the data D-OUT output to the data processor 12. The echo signals are also fed to a low-pass filter RSSI-LPF, then to a buffer RSSI-BUFF and digitized by an analog-to-digital converter RSSI-ADC. Finally, they are fed to the data processor as part of the output signal D-OUT.

A timing generator TMG-GEN generates all signals needed for the transmitter and receiver, such as the transmit signals, transmit enable, and the local oscillator quadrature signal for the mixer. The frequency of the pulses emitted by the transducer is selected to maximize resolution while maintaining adequate profiling range. In the present, a frequency of about 1.23 MHz is preferred. A transmitter amplifier XMT-AMP acts as a power driver which buffers the logic level signal generated by the timing generator, and drives a transmitter output transformer XMT-XFMR, the transmit transformer also provides isolation between the electronic processing unit and the transducer.

The transmit current is monitored by a current transformer CURR-XFMR. Its output signal is scaled and digitized by an analog-to-digital converter CURR-ADC and is used as part of a built-in self-test by the data processor. All timing generator setups are fully programmable, and are downloaded by the data processor to the timing generator's on an internal RAM.

The data processor is able to read back, the timing setup data and the digitized current sensed data.

Figure 6:
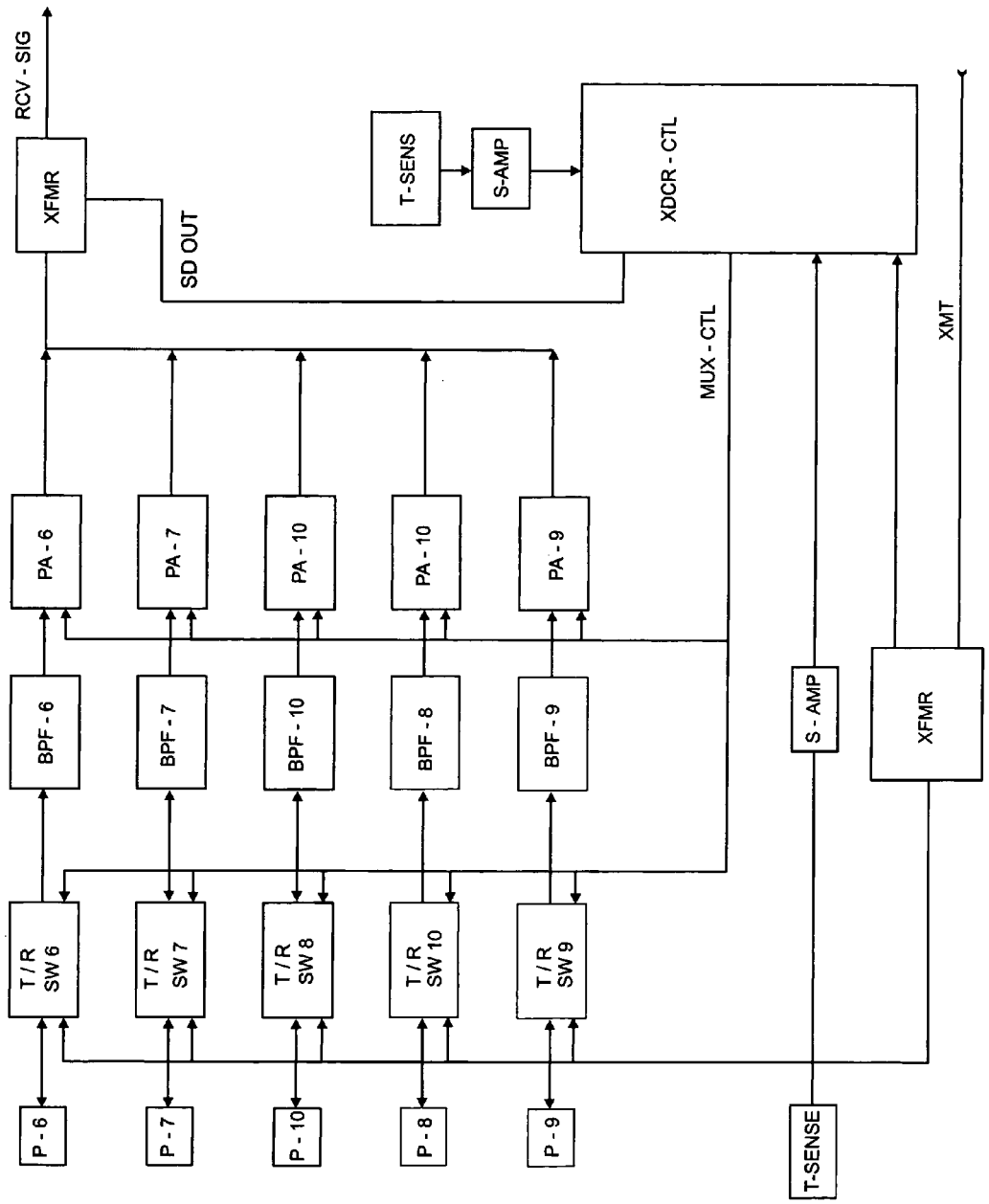
FIG. 6 is a block diagram of the transducer circuitry.

The transducer illustrated in FIG. 6 includes a signal transmit and receive multiplexer controlled by the electronic processing unit. The transmit signal generated by the timing generator TMG-GEN of the electronic processing unit passes through a coupling transformer XFMR which provides isolation and impedance matching. The signal is then multiplexed to one of the five beams by a selectable transmit/receive switch T/R-SW6–T/R-SW10. At the end of the transmitting phase, the multiplexer is deselected. As the echo signal is received from the Piezoelectric ceramics P-6 through P-10, it passes through the switch and one of the selected band pass filters BPF-6 through BPF-10 then to a preamplifier PA-6 through PA-10 and is converted to a differential signal by a wide band signal transformer XFMR before being fed to the electronic control unit. A thermiistor T-SENSE is used to measure the transducer's ambient temperature. The temperature signal is scaled and buffered by an amplifier S-AMP, digitized by the transducer control XDCR-CTL and fed to the electronic control unit.

The following simplified formula of the acoustic theory governing backscatter from particles suspended in the water column identifies the main factors that contribute to the determination of suspended solids concentration from the intensity data.

$$E = SL + SV + \text{Constant} - 20\log(R) - 2\alpha_w R \quad (1)$$

where:

$E$ = echo intensity,
$SL$ = transmitted power,
$SV$ = backscatter intensity due to the particles suspended in the water column,
$\alpha_w$ = a coefficient describing the absorption of energy by the water,
$R$ = the distance from the transducer to the measurement bin.

The echo intensity E measured by the system is a relative intensity, coming from direct measurement of the pressure amplitude of the return signal. Although the system will clearly recognize variations of echo intensity, it cannot determine the exact amount of backscatter intensity that is due solely to the presence of solids. Other factors that contribute to the final intensity must be removed.

The term 20log R is a simple geometric function to account for the spherical spreading of the beam. This term can be further refined to include a near-field correction to the assumption of spherical spreading. Accurate knowledge of the velocity of sound is essential for determination of the range to a given measurement bin. The system computes a range based on the measured time and a sound velocity. Sound velocity is computed by using a user-defined salinity (assumed to be 0 for the sewer environment) and the temperature measured at the sensor head. This speed of sound is assumed by the method described here to be constant throughout the water column. This is a safe assumption in sewer environments as the depth of the flow is limited and the flow is well mixed.

It is not possible to make direct comparisons between the measurements made by different instruments unless the instruments have been calibrated in the field or the laboratory to establish their performance characteristics. The terms SL and Constant account for these differences and also deal with the characteristics of the suspended load. Understanding the manner in which instrument performance characteristics affect the data and correcting for these differences through field calibrations is key to the measurement method. This method makes use of the measured relative backscattered intensities and uses site-specific calibrations to compensate for such variations and determine a concentration of suspended solids.

The final two terms $a_W$ and SV, refer to the absorption of acoustic energy by the water and the relative backscatter intensity. Acoustic energy is absorbed by water as it passes through it, and $a_W$ is a measure of the amount of energy lost in this process. SV is the term we are interested in—the amount of energy that is backscattered by the presence of solids in the water column. An increase or decrease in the amount of solids will affect the value of SV. An additional term not included in Equation 1 must also be accounted for. This term describes the attenuation of the acoustic signal due to scattering and absorption by the suspended load.

To actually derive the mass concentration of total suspended solids TSS in the water from the measured intensity, one must determine the true backscattered sound intensity due to the presence of the solids. It can be shown that the relationship between the two parameters is as follows:

$$M(r) = (K < P_{\text{rms}} > r)^2 \frac{<a_s> \rho_s}{<f>^2} e^{4r(\alpha_w + \alpha_s)} \quad (2)$$

where: $M(r)$ = mass concentration per unit volume at range $r$
$K$ = a constant for the acoustic system
$P_{\text{rms}}$ = backscattered pressure
$a_s$ = particle radius
$\rho_s$ = particle density
$<f>$ = particle form function
$\alpha_w$ = water attenuation coefficient
$\alpha_s$ = solids attenuation cefficient In this equation, the expected mass concentration, M(r) is a function of the sediment attenuation coefficient $a_S$, which defines how the presence of solids attenuates the return signal. Both of these parameters are unknown. To provide a solution to this, it is necessary to use a numerical method. Computation of the mass concentration is performed without using a value of $a_S$. The resulting value of M(r) is used to compute a value for $a_S$. This computation process is iterated in the bin nearest to the sensor to derive final values of both sediment attenuation and mass concentration. This method is then applied in a step-wise manner along the successive bins of the profile.

The method proposed here to allow for the measurement of solids concentration on site, accomplishes this by using a simplified version of the above-expression.

The method proposed here to allow for the measurement of solids concentration on site, accomplishes this by using a simplified version of the above-expression:

$$\text{Log}_{10} M(r) = K_s + S[dB + 2r(\alpha_w + \alpha_s)] \quad (3)$$

wherein:
dB is now the measured relative backscatter intensity, corrected for spherical spreading and any applicable near field effects. S is the relative backscatter coefficient that defines the relationship between solids concentration and particle size. $K_S$ is the site and sensor specific constant that corrects for the individual characteristics of a specific instrument at a given site. The other terms are as in Equation 2 and and represent intensity attenuation by the presence of solids ($a_S$) and water absorption ($a_W$).

The amount of sound energy which is lost, or attenuated, due to the absorption by water has been found to depend on the frequency of the sound waves (i.e., of the instrument), and the salinity and the temperature of the water as follows:

$$\alpha_w = \frac{f}{91500} \left[ \frac{1.86 S f_T f}{(f_T^2 + f^2)} + \frac{2.86 f}{f_T} \right] \quad (4)$$

where: $\alpha_w$ = the water absorption coefficient in Nepers/$m$
$f$ = the instrument frequency, in MHz
$S$ = the salinity in ppt.

The term, ft, is called the Relaxation Frequency and is given by the following expression:

$$f_T = 21.9 \times 10^{(6-\frac{1520}{273+T})} \quad (5)$$

where:

T is the water temperature in degrees Celsius.

Using these formulae, the attenuation of the signal due to water absorption, per meter, may be computed and hence, using the slant length of the bin, the total attenuation of sound through each measurement interval, or "bin", can be derived.

When sound passing through the water column strikes particles of suspended solids, the energy is attentuated both by scattering and absorption by the solid media. The degree of scattering depends on the relationship between the frequency and the size of the particle. Frequency may be expressed in terms of the Wave Number, k, where:

$$k = \frac{2\pi f}{V_s} \quad (6)$$

where: $f$ = the instrument frequency in Hertz $V_s$ = the velocity of sound in m/s.

where:

f=the instrument frequency in Hertz $V_s$=the velocity of sound in m/s.

When the value of the product $ka_S$ (where $a_s$ is the particle radius) is well below 0.5, Rayleigh scattering occurs. This is the range normally found during suspended sediment measuring conditions. The sediment constant 51, is given by:

$$\zeta_1 = \frac{K_\alpha}{\rho_s} k^4 a_s^3 \quad (7)$$

where $\rho_s$ = the density of the sediment in kg/m³

$K_\alpha$ = a term relating to compressibility and density (normal value 0.18)

where:

$\rho_s$=the density of the sediment in kg/m³

$K_\alpha$=a term relating to compressibility and density (normal value 0.18)

The actual sediment attenuation per meter due to scattering, $a_1$ (Nepers/m), by the solids in a region at range, r, and with a mass concentration of $M_r$ (kg/m³) is then given by:

$$a_1 = M_r \times \zeta_1 \quad (8)$$

Acoustic energy is also absorbed by sediment in the water column. The following expression (Urick, 1948) is used to determine the sediment attenuation per meter due to this absorption, $a_2$ (Nepers/m):

$$\alpha_2 = \frac{M_r k(\sigma - 1)^2}{2\rho_s} \left[ \frac{s}{s^2 + (\sigma + \delta)^2} \right] \quad (9)$$

where: $\sigma = \frac{\rho s}{\rho w}$ $s = \frac{9}{4\beta a_s}\left[1 + \frac{1}{\beta a_s}\right]$ $\beta = \left[\frac{kV_s}{2u_{iv}}\right]^{\frac{1}{2}}$ and : $\rho_s$ = the density of the solid particles $\rho_w$ = the density of the water $v_w$ = the kinematic viscosity of the water.

The above-expressions are valid for values of the product $ka_S$, being much less than unity. This is the region where attenuation due to scattering becomes negligible and viscous absorption begins to dominate.

The method combines the attenuation due to scattering and absorption into a single Sediment Attenuation Coefficient SAC. The SAC can either be defined by the user or can be computed by the processing softare using a nominal, or "effective", particle size in combination with assumed values for particle specific gravity (2.7) and compressibility (0.18). In both cases, the input values are inevitably estimates and must be refined by iteration within the software's Calibration Module.

It is almost impossible, in practice, to calculate from first principles the sediment attenuation coefficient for a natural population of sediment. The approach used in the software is a pragmatic approach in which workable values of the coefficient are established using actual observational data. It therefore, becomes somewhat academic as to whether or not the input values of, for example, particle size and compressibility are correct.

The computer program CP controlling the data processor carries out all of the computations required to derive sediment concentrations from measured backscatter intensity, according to the simplified Equation 3 and a value for sediment attenuation derived by calibration. The program imports the backscatter data (expressed in instrument counts) and ancillary information (e.g., temperature, salinity, etc.) from raw system data files. The user may either input specific site calibrations values (e.g., values for S and Ks) on the keyboard or have the program determine these values from entered data. The user also input values for TSS that were measured by taking samples of water and having them analyzed by a laboratory for TSS values. These sample are taken concurrently with the system data so that a direct calibration between system-measured values and actual values can be determined.

The program then takes the raw measured data from the first valid measurement bin of each transducer. It calculates the various required parameters and solves Equation 3, using the iterative routine, to find the suspended sediment concentration in the first whole bin and in the interval between the transducers and the first bin (where the system cannot obtain data). The computed solids concentrations and sediment attenuation are then fed into the system again in order to make the relevant corrections in the next bin, which is then solved using a similar iterative process. The procedure is repeated until the last whole bin has been solved. The software then moves on to the next ensemble of data.

Following this, the program displays the calculated concentrations and compares them to the actual measured concentrations. Errors between the two data sets, calculated then actual, are also displayed as functions of depth and concentration. The user then adjusts the different parameters (S, Ks, and the SAC) to improve the correlation between data sets. As this is an iterative process, and some parameters are initially given seed values, the user adjusts the parameters to increase the correlation between the two data sets and reduce the errors to zero, while observing the results of their actions in real-time.

The method can be utilized in the sanitary and combined sewer environment, and can provide both historical and real-time measurement of TSS in addition to flow measurement. This will allow users to measure total mass transport of solids within sanitary sewer systems as well as the volume transport of water. The method described here uses data from multiple beams to accomplish this. The method has the ability to look at the spatial distribution of solids concentration in the depth of flow as well as total solids concentration.

What is claimed is:

1. An apparatus, for measuring concentration, distribution and flow of solids suspended in a flowing liquid, which comprises:
   a transmitter emitting at least one directional beam of an acoustical waveform;
   at least one detector receiving echo signals of said waveform backscattered from said solids;
   means for gathering measured intensity values of said echo signals;
   means for measuring Doppler frequency shifts of said echo signals; and
   data processing equipment comprising means for translating said intensity values into concentration values of said solids, and means for interpreting said frequency shifts into flow measurements of said solids.

2. The apparatus of claim 1, wherein said flowing liquid is contained in a conduit having a directional flow, and said transmitter and detector are located inside said conduit.

3. An apparatus, for measuring concentration, distribution and flow of solids suspended in a flowing liquid, which comprises:
   a transmitter emitting at least one directional beam of an acoustical waveform;
   at least one detector receiving echo signals of said waveform backscattered from said solids;
   means for gathering measured intensity values of said echo signals;
   means for measuring Doppler frequency shifts of said echo signals;
   data processing equipment comprising means for translating said intensity values into concentration values of said solids, and means for interpreting said frequency shifts into flow measurements of said solids;
   wherein said flowing liquid is contained in a conduit having a directional flow and said transmitter and detector are located inside said conduit; and
   said transmitter emits at least a first pair of said beams from substantially the same location, a second beam in said pair being aimed downstream from a first beam and at a longitudinal angle from said first beam.

4. The apparatus of claim 3 which further comprises a second of said pair of beams aimed at a transversal angle from said first pair of beams.

5. The apparatus of claim 4 which further comprises means for generating samplings of said echo signals corresponding to discrete volumes of said liquid distributed along said beams.

6. The apparatus of claim 5, wherein said means for translating comprises means for calibrating said intensity values by imputing site specific environmental information.

7. The apparatus of claim 6, wherein said data processing equipment further comprises program means for adjusting at least one calibration parameter in translating intensity value from one of said volumes using values obtained from another volume along the same beam.

8. The apparatus of claim 6, wherein said means for calibrating comprises means for automatically entering information, and means for manually entering information.

9. The apparatus of claim 6, wherein said means for translating further comprises means for entering concentration values obtained from a previous measurement.

10. The apparatus of claim 9, wherein said site specific environmental information comprises water temperature, salinity and acoustical system constants, and echo signal assignment ratio between concentration and particle size.

11. The apparatus of claim 5, wherein said means for translating comprise means for computing a mass concentration of solid M® per unit volume at a range r according to the formula:

$$Log_{10}M(r)=K_S+S[dB+2r(\alpha_W+\alpha_S)]$$

wherein
   $K_S$ is a site and instrument constant,
   S is a relative backscattered coefficient defining the relationship between solid concentration and particle size,
   dB is the measured relative backscattered intensity,
   $\alpha_W$ is a water attenuation coefficient, and
   $\alpha_S$ is an attenuation coefficient due to the presence of solids.

12. The apparatus of claim 6, wherein said means for translating further comprise:
   means for using $M_r$ values obtained in connection with one of said volumes to compute said attenuation coefficient $\alpha_S$; and
   means for imputing said $\alpha_S$ value in translating said intensity value into an M® value for the next of said volume farther away from said transmitter.

13. An apparatus, for measuring concentration distribution and flow of solids suspended in a flowing liquid, which comprises:
   a transmitter emitting at least one directional beam of an acoustical waveform;
   at least one detector receiving echo signals of said waveform backscattered from said solids;
   means for gathering measured intensity values of said echo signals;
   means for measuring Doppler frequency shifts of said echo signals;
   data processing equipment comprising means for translating said intensity values into concentration values of said solids, and means for interpreting said frequency shifts into flow measurements of said solids; and
   means for generating samplings of said echo signals corresponding to discrete volumes of said liquid distributed along said beam.

14. The apparatus of claim 13, wherein said means for translating comprises means for calibrating said intensity values by imputing site specific environmental information.

15. The apparatus of claim 14, wherein said site specific environmental information comprises water temperature, salinity and acoustical system constants, and an echo signal assignment ratio between concentration and particle size.

16. The apparatus of claim 14, wherein said data processing equipment further comprises program means for adjusting at least one calibration parameter in translating intensity value from one of said volumes using values obtained from another volume along the same beam.

17. The apparatus of claim 13, wherein said means for translating further comprises means for entering suspended solids concentration values obtained from a previous measurement.

18. The apparatus of claim 14, wherein said means for calibrating comprises means for automatically entering information, and means for manually entering information.

19. The apparatus of claim 13, wherein said means for translating comprise means for computing a mass concentration of solid M® per unit volume at a range r according to the formula:

$$Log_{10}M(r)=K_S+S[dB+2r(\alpha_W+\alpha_S)]$$

wherein $K_S$ is a site and instrument constant,

S is a relative backscattered coefficient defining the relationship between solid concentration and particle size, dB is the measured relative backscattered intensity, $\alpha_W$ is a water attenuation coefficient, and $\alpha_S$ is an attenuation coefficient due to the presence of solids.

20. The apparatus of claim 19, wherein said means for translating further comprise:

means for using M® values obtained in connection with one of said volumes to compute said attenuation coefficient $\alpha_S$; and, means for imputing said $\alpha_S$ value in translating said intensity value into an M® value for the next of said volume farther away from said transmitter.

21. A method for measuring concentration, distribution and flow of solids suspended in a flowing liquid, which comprises:

emitting at least one directional beam of an acoustical waveform across said liquid;

receiving range-gated samplings of echo signals of said waveform backscattered from said solids;

gathering measured intensity value of said samplings signals;

measuring Doppler frequency shifts of said samplings signals;

translating said intensity values into estimated concentration values of said solids; and interpreting said frequency shifts into flow measurements of said solids.

22. The method of claim 21, wherein said flowing liquid is contained in a conduit having a directional flow, and said transmitter and detector are located inside said conduit.

23. A method for measuring concentration, distribution and flow of solids suspended in a flowing liquid, which comprises:

emitting at least one directional beam of an acoustical waveform across said liquid;

receiving echo signals of said waveform backscattered from said solids;

gathering measured intensity value of said echo signals;

measuring Doppler frequency shifts of said echo signals;

translating said intensity values into concentration values of said solids;

interpreting said frequency shifts into flow measurements of said solids;

wherein said flowing liquid is contained in a conduit having a directional flow, and said transmitter and detector are located inside said conduit; and said emitting comprises transmitting at least a first pair of said beams from substantially the same location, a second beam in said pair being aimed downstream from a first beam and at a longitudinal angle from said first beam.

24. The method of claim 23 which further comprises emitting a second of said pair of beams aimed at a transversal angle from said first pair of beams.

25. The method of claim 24 which further comprises samplings of said echo signals corresponding to discrete volumes of said liquid distributed along said beams.

26. The method of claim 25, wherein said translating comprises calibrating said intensity values by imputing site specific environmental information.

27. The method of claim 26, wherein said data processing equipment further comprises program adjusting at least one calibration parameter in translating intensity value from one of said volumes using values obtained from another volume along the same beam.

28. The method of claim 26, wherein said calibrating comprises automatically entering information, and manually entering information.

29. The method of claim 25, wherein said translating further comprises entering concentration values obtained from a previous measurement.

30. The method of claim 29, wherein said site specific environmental information comprises water temperature, salinity and acoustical system constants, and echo signal assignment ratio between concentration and particle size.

31. The method of claim 25, wherein said translating comprise computing a mass concentration of solid M® per unit volume at a range r according to the formula:

$$Log_{10}M(r)=K_S+S[dB+2r(\alpha_W+\alpha_S)]$$

wherein $K_S$ is a site and instrument constant,

S is a relative backscattered coefficient defining the relationship between solid concentration and particle size, dB is the measured relative backscattered intensity, $\alpha_W$ is a water attenuation coefficient, and $\alpha_S$ is an attenuation coefficient due to the presence of solids.

32. The method of claim 31, wherein said translating further comprise:

using $M_r$ values obtained in connection with one of said volumes to compute said attenuation coefficient $a_S$; and imputing said $a_S$ value in translating said intensity value into an M® value for the next of said volume farther away from said transmitter.

33. A method for measuring concentration, distribution and flow of solids suspended in a flowing liquid, which comprises:

emitting at least one directional beam of an acoustical waveform across said liquid;

receiving echo signals of said waveform backscattered from said solids;

gathering measured intensity value of said echo signals;

measuring Doppler frequency shifts of said echo signals;

translating said intensity values into concentration values of said solids;

interpreting said frequency shifts into flow measurements of said solids; and generating samplings of said echo signals corresponding to discrete volumes of said liquid distributed along said beam.

34. The method of claim 33, wherein said translating comprises calibrating said intensity values by imputing site specific environmental information.

35. The method of claim 34 which further comprises adjusting at least one calibration parameter in translating intensity value from one of said volumes using values obtained from another volume along the same beam.

36. The method of claim 34, wherein said calibrating comprises automatically entering information, and manually entering information.

37. The method of claim 33, wherein said translating further comprises entering suspended solids concentration values obtained from a previous measurement.

38. The method of claim 37, wherein said site specific environmental information comprises water temperature, salinity and acoustical system constants, and echo signal assignment ratio between concentration and particle size.

39. The method of claim 33, wherein said translating comprise computing a mass concentration of solid M® per unit volume at a range r according to the formula:

$$Log_{10}M(r)=K_S+S[dB+2r(\alpha_W+\alpha_S)]$$

wherein $K_S$ is a site and instrument constant,

S is a relative backscattered coefficient defining the relationship between solid concentration and particle size, dB is the measured relative backscattered intensity, $\alpha_W$ is a water attenuation coefficient, and $\alpha_S$ is an attenuation coefficient due to the presence of solids.

40. The method of claim 39, wherein said translating further comprise:

using $M_r$ values obtained in connection with one of said volumes to compute said attenuation coefficient $\alpha_S$; and imputing said $\alpha_S$ value in translating said intensity value into an M® value for the next of said volume farther away from said transmitter.

* * * * *